US006482959B1

(12) United States Patent
Baloghne et al.

(10) Patent No.: US 6,482,959 B1
(45) Date of Patent: Nov. 19, 2002

(54) PROCESS FOR THE STEREOSELECTIVE REDUCTION OF α,β-UNSATURATED KETONES

(75) Inventors: Kardos Zsuzsanna Baloghne, Budapest (HU); Nandor Benno, Budapest (HU); Povarny Magdonla Beresne, Budapest (HU); Gyula Dalmadi, Budapest (HU); Katalin Ebinger, Budapest (HU); Laszlo Forro, Budapest (HU); Geza Galambos, deceased, late of Budapest (HU), by Eva Galambos, Attila Galambos, heir & legal representative; Felix Hajdu, Budapest (HU); Istvan Hermecz, Budapest (HU); Geza Lukacs, Budapest (HU); Karoly Mozsolits, Sopron (HU); Szigeti Katalin Polikne, Budapest (HU); Judit Sebestyen, Budapest (HU); Tobor Szabo, Budapest (HU); Zoltan Szeverenyi, Budapest (HU); Ervin Vajda, Budapest (HU); Gabor Vankai, Budapest (HU); Pal Vofely, Budapest (HU)

(73) Assignee: Chinoin Gyógyszer és Vegyészeti Termékek Gyára Rt., Budapest (HU)

( * ) Notice: Subject to any disclaimer, the term of this patent is extended or adjusted under 35 U.S.C. 154(b) by 0 days.

(21) Appl. No.: 09/091,481

(22) PCT Filed: Dec. 18, 1996

(86) PCT No.: PCT/HU96/00079

§ 371 (c)(1),
(2), (4) Date: Jun. 27, 2000

(87) PCT Pub. No.: WO97/22602

PCT Pub. Date: Jun. 26, 1997

(30) Foreign Application Priority Data

Dec. 20, 1995 (HU) .............................. 9503665

(51) Int. Cl.⁷ ............................................ C07D 307/00
(52) U.S. Cl. ...................................................... 549/305
(58) Field of Search ......................................... 549/305

(56) References Cited

U.S. PATENT DOCUMENTS

| 3,970,684 A | 7/1976 | Crabbé et al. ............... 260/468 |
| 3,974,183 A | 8/1976 | Corey |
| 4,739,078 A | 4/1988 | Pearlman |

FOREIGN PATENT DOCUMENTS

| EP | A10136779 | 4/1985 |
| EP | A10219580 | 4/1987 |
| EP | 0289349 A1 | 2/1988 |
| EP | 0435443 A2 | 7/1991 |
| EP | 0455448 A2 | 11/1991 |
| EP | 0467564 A2 | 1/1992 |
| EP | 0219580 * | 4/2000 |
| HU | 175889 * | 3/1981 |

OTHER PUBLICATIONS

Iwamoto et. al., "Studies on prostaglandins. VI. Synthesis of 16(S)–methyl–20–methoxy–PGE2 (YPG–209) having oral bronchodilator activity and its analogs", Chemical & Pharmaceutical Bulletin, vol. 28, No. 5, 1980.*

*Chemical Abstracts*, vol. 95 p. 6616 (1981).

Journal of the American Chemical Society, vol., 109, Dec. 9, 1987, A Stable and Easily Prepared Catalyst for the Enantioselective Reduction of Ketones. Application to Multistep Syntheses. pp. 7925–7926.

Prostaglandins Intermediates. Reduction of (E)–Oxolactone by Means of a Chiral Phase Transfer Catalyst. C. Passarotti et al, pp. 195–198.

Efficient Generation of the 15S Configuration in Prostaglandin Synthesis. Attractive Interactions in Stereochemical Control of Carbonyl Reduction, Cyril Tang, et al, Nov. 29, 1972, pp. 8616–8618.

New Reagents for Steroselective Carbonyl Reduction. An Improved Synthetic Route to the Primary Prostaglandins, vol. 93, Mar. 24, 1971 No. 6, pp. 1491–1494.

Diisobutylaluminum 2–6–Di–t–butyl–4–methylphenoxide. Novel.

(I)

(II)

(III)

Synthetic Applications of the Enatioselective Reduction by Binaphthol–Modified Lithium Aluminum Hydride Reagents, R. Noyori et al, pp. 6717–6725.
Synthetic Communication, 9(6), 483–486, (1979), Di–Isobornyloxyaluminum Isopropoxine–A New Highly Selective Meerwein–Pondorf–Verley Reagents, J. Hutton, Imperial Chemical Industries, Ltd., Pharmaceutical Division, Macclesfield, Cheshire, SK1io, 4TG, pp. 483–486.
Studies on Prostaglandins VI. Syntheses of 169S)–Methyl–20–Methoxy–PGE, (YPG–209) having Oral Bronchodilator Activity and its Analogs, Hidenori Iwamoto et al, pp. 1422–1431.
N. (Methanesulfonyl)–16–phenoxyoprostaglandincarboxamides: Tissue–Selective Uterine Stimulants, Thomas K, Schaef et al J. Medical Chem. 1981, 24, 1353–1359.
Stero–Controlled Synthesis of Prostaglandins F2 and E2 (dl), J. Alan Webber et al, pp. 5675–5677.
Synthetic Communications, 19(1&2), 245–255 (1989), A Practical Route for the Syntheses of Prostaglandin D2 Metabolites, Chandra Prakash et al.
Synthetic Communications, 9(9), 799–808 (1979) The Reduction of Prostaglandin Intermediates Using Aumino Hydride Reagents, J. Hutton et al.
Synthetic Communication, 4(4), 211–213, (1974), Reduction of Prostaglandin Enone Intermediates with Aluminum Isopropoxide, Jean Bowler et al, pp. 211–213.
J. Org. Chem. vol. 44, No. 8, 1979 pp. 1363, George R. Newkome et al, Department of Chemistry, Diisobutylaluminum 2, 6–Di–tert–butyl–4–methlyphenoxide. Novel Sterselective Reducing Agent for Prostaglandin Synthesis.
Szabadalmi Leiras 175889, C 07 D 307/93, Mar. 31,1981.

\* cited by examiner

*Primary Examiner*—Alan L. Rotman
*Assistant Examiner*—Binta Robinson
(74) *Attorney, Agent, or Firm*—Birch, Stewart, Kolasch & Birch, LLP

(57) ABSTRACT

A process for the preparation of α,β-unsaturated alcohols of general formula (I),

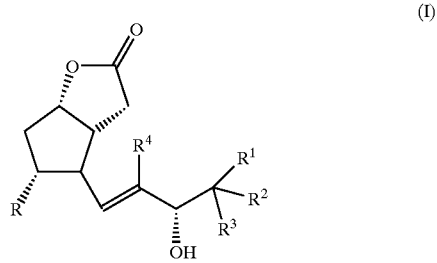

(I)

wherein
R means an alkyl group of 1–4 carbon atoms, or benzoyloxy group optionally substituted with a phenyl group;
$R^1$ means a hydrogen atom or an alkyl group of 1–4 carbon atoms,
$R^2$ means a hydrogen atom or an alkyl group of 1–4 carbon atoms;
$R^3$ means an alkyl group of 1–6 carbon atoms optionally substituted by phenyl group or cycloalkyl group of 5–7 carbon atoms; or a phenoxy group optionally substituted by a halogen atom, or a cycloalkyl group of 5–7 carbon atoms;
$R^4$ means a hydrogen atom or a halogen atom
whereby at α,β-unsaturated ketones of general formula (II) wherein the

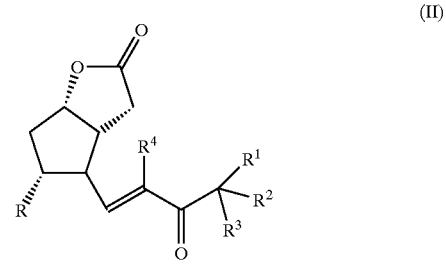

(II)

meanings of R, $R^1$, $R^2$, $R^3$, and $R^4$ are as given above—is diastereoselectively reduced with a borohydride type compound in an aprotic solvent, in the presence of an inorganic substance dissolublein the reaction mixture and having particle size from 0.01 micrometer to 10000 micrometer and optionally from the resulting mixture of epimeric α,β-unsaturated alcohols of general formula (I) and (III)

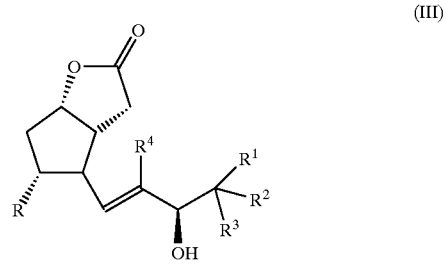

(III)

meanings of R, $R^1$, $R^2$, $R^3$, and $R^4$ are as given above—the α,β-unsaturated alcohol of general formula (I) is separated by methods known.

18 Claims, 1 Drawing Sheet

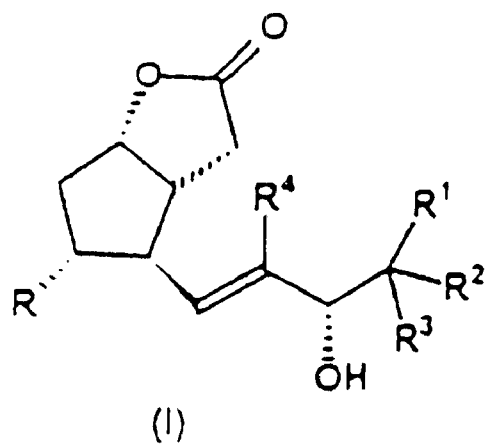
(I)
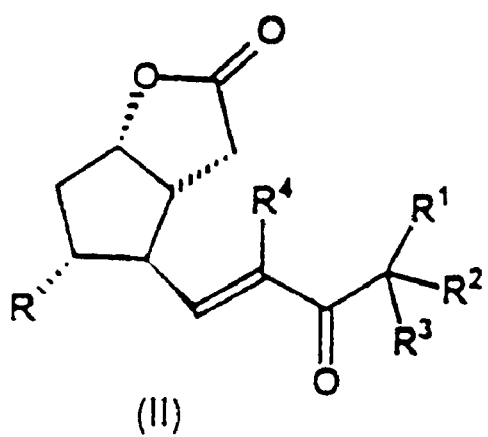
(II)
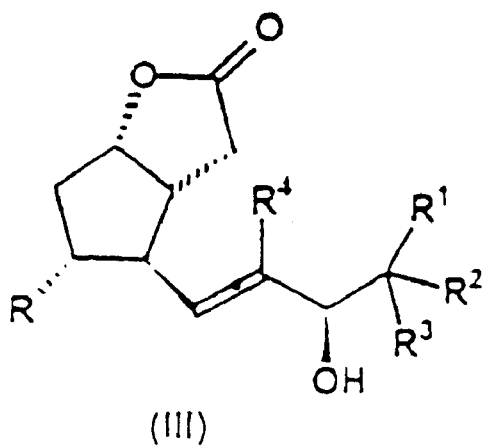
(III)

PROCESS FOR THE STEREOSELECTIVE REDUCTION OF α,β-UNSATURATED KETONES

This application is the national phase under 35 U.S.C. §371 of prior PCT International Application No., PCT/HU96/00079, which has an International filing date of Dec. 18, 1996, which designated the United States of America, the entire contents of which are hereby incorporated by reference.

The present invention relates to a new process for the preparation of α,β-unsaturated alcohols by the diastereoselective reduction of α,β-unsaturated ketones. Representative reactants and products of the present invention are depicted in FIG. 1, with compound (I) depicting representative product α,β-unsaturated alcohols, compound (II) depicting representative α,β-unsaturated ketones, and compound (III) depicting representative epimers of product α,β-unsaturated alcohols (I).

α,β-Unsaturated alcohols of general formula (I) are important key intermediates of prostaglandine derivatives used in veterinary and human medicine.

The synthesis of these compounds is carried out most frequently by reduction of α,β-unsaturated ketones of formula (II), when a mixture of α,β-unsaturated alcohols of formula (I) and the epimers of formula (III):

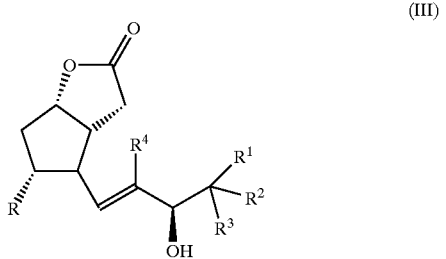

(III)

is formed. These two epimer alcohols are separated directly or during some further steps of chemical transformation, usually by chormatographic.

The synthesis of these compounds is carried out most frequently by reduction of α,β-unsaturated ketones of formula (II), when a mixture of α,β-unsaturated alcohols of formula (I) and their epimers of formula (III):

The reduction of the keto group of α,β-unsaturated ketones of general formula (II) was studied in detail in order to enhance the yield and ratio of α,β-unsaturated alcohols of general formula (I) and at the same time to avoid saturation of the α,β-double bond. In the prior art the reduction of α,β-unsaturated ketones of general formula (II) was realized by using borohydride reagents containing a bulky, possibly optically active substituent and in a solvent having ether character (e.g. in tetrahydrofurane, or in a mixture of tetrahydrofurane, diethyl-ether and pentane), at a temperature from −78° C. to −130° C., where the ratio of α,β-unsaturated epimer alcohols of general formula (I) and of general formula (III) is altered between 1:2–4.5 (J. Am. Chem. Soc. 95, 1491 (1971); J. Am. Chem. Soc. 94, 8616 (1972); U.S. Pat. No. 3,974,183 HU-PS-175.889 Hungarian Patent ). As reducing agents commercially not available lithium—diisopinocam—phenyl-tert-butyl-borohydride, lithium-2-thexyl-8-methyl-2-borobicyclo[3,3,1]nonyl-borohydride, lithium tricyclopentyl-borohydride or lithium-diisobutyl-tert-butyl-aluminumhydride and L-selektride® (lithium-tri-sec-butyl-borohydride) (all containing bulky groups) were used among others.

Some representatives of α,β-unsaturated ketons of general formula (II) were reduced by applying zinc borohydride too, in 1,2-dimethoxyethane at 0° C. and at room temperature, where the epimers of general formula (I) and general formula (III) were formed in an 1:1 ratio (J. Am. Chem. Soc. 91, 5675 (1969); J. Am. Chem. Soc. 94, 8616 (1972); U.S. Pat. No. 3,970,684;

Using sodium borohydride in ethanol at −30° C. or lithium-trialkyl-borohydride at a temperature lower than −90° C. as reducing agents, the ratio of the epimeric α,β-unsaturated alcohols of general formula (I) and of general formula (III) fluctuated between the ratios of 50:50 and 60:40 (J. Am. Chem. Soc. 94, 8616 (1972); EP-A-435,443; EP-A-455,448; EP-A-467,564; J. Med. Chem. 24, 1353 (1981). Using sodium borohydride as reducing agent the selectivity of the reduction could be increased when the reduction was carried out at −78° C. in methanol or in a mixture of methanol and dichloromethane, in the presence of cerium (III) chloride (EP-A-219,580; U.S. Pat. No. 4,739, 078). Using borane as the reducing agent in the presence of 5–10% air and humidity sensitive oxazaborolydines, a far more favourable diastereomer ratio could be achieved (J. Am. Chem.Soc. 109, 7925 (1987)), but this method can not be applied on a larger scale. Using diisobutyl-aluminum-(2, 6-di-tert.butyl-4-methyl phenoxide) (J. Org. Chem. 44, 1363 (1979); Bull.Chem.Soc. Japan 54, 3033 (1981)) at −78° C.; aluminium-isopropoxide in nitrogen atmosphere and in hot toluene (Synthetic Communications 4, 211 (1974)), di(isobornyloxy)-aluminium-isopropoxide or other modified lithium-aluminium-hydrides (J.Am.Chem.Soc. 106, 6717 (1984); Synthetic Communications 9, 799 (1979); Synthetic Communications 9, 483 (1979)) did not represent any advantage either because of difficulties of preparing these reagents, their sensitivity, and/or the costs of preparing them.

Under the conditions of catalytic hydrogenation, e.g. using charcoal containing palladium catalyst of 5% metal content, the carbon-carbon double bond of the α,β-unsaturated ketons of general formula (II) saturates without the reduction of the ketone group (EP-A-289,349; Synthetic Communications 19, 245 (1989); EP-A-435,443.

It is the object of this invention to provide an industrially feasible process, which is suitable at room temperature and without applying special additives, extreme conditions and reagents for the preparation of compounds of general formula (I) by diastereomeric reduction of ketones of general formula (II) in higher yields them in any known processes. The base of this new process achieving this object is the unexpected finding that α,β-unsaturated alcohols of general formula (I)—wherein R means an alkyl group containing 1–4 carbon atoms, or in a given case benzoyl group substituted with phenyl group; $R^1$ means hydrogen atom or an alkyl group containing 1–4 carbon atoms; $R^2$ means hydrogen atom or alkyl group containing 1–4 carbon atoms; $R^3$ means in a given case an alkyl group containing 1–6 carbon atoms substituted with phenyl group or with cycloalkyl group containing 5–7 carbon atoms, or in a given case phenoxy group substituted with halogen atom or a cycloalkyl group containing 5–7 carbon atoms, $R^4$ means hydrogen atom or halogen atom—are formed diastereoselectively upon reduction of α,β-unsaturated ketones of general formula (II)—wherein the meanings of R, $R^1$,$R^2$,$R^3$, and $R^4$ are as given above—if alkali borohydrides of small space demand are applied and the reaction is carried out in a heterogen phase, in an aprotic solvent in the presence of inorganic substances which are dissoluble in the reaction mixture and their particle sizes are small.

According to our experiences within the conditions described above and within the temperature range of −10° C.

and +30° C. diastereoselectivity barely fluctuated. Thus the reaction can be carried out at about the room temperature. The term of inorganic substances dissoluble in the reaction mixture and having small particle sizes means farourably silicium compounds and/or aluminium compounds or mixtures thereof These are preferably the silica gels, different types of aluminium oxide, in the first place the "active" aluminium oxides which can be acidic, basic, or neutral in their reaction, the adsorptive capacity of which can be determined by the Brockmann scale./Römp Chemical Encyclopedia Vol. I. p. 116–117 (Müszaki Könyvkiadó=Technical Publishing House. Bp.1982)/. The term of silica gels which are useful in the claimed new process means silicic acid gels as defined in Römp Chemical Encyclopedia Vol.II. P. 977–978 /Müszaki Könyvkiadó, Budapest. 1982/. These are for example Silica gel 60, Silica gel G. "Small particle sizes" means 0.01–10000 micrometer preferably the particle size range is from 1 µm to 1000 µm.

Applicable aprotic solvents preferably halogenated hydrocarbons as chlorobenzene, methylene chloride, carbon tetrachloride, chloroform, 1,1,2,2-tetrachloroctane; alkane carboxylic acid esters as ethyl acetate, methyl acetate, methyl propionate; hydrocarbons as xylene, or toluene; alkyl nitriles as acetonitrile; ethers as tetrahydrofurane or diethyl-ether can be used. If we use ethanol as solvent for the reduction, or we carry out the reduction without the presence of silica gel, then diasteroeselectivity decreases substantially. The presence of small quantity of alcohol of short carbon chain e.g. methanol however facilitates the reaction.

As borohydrides of small space demand can be applied preferably their commercially available representatives sodium[trimethoxy-borohydride], lithium borohydride, sodium borohydride, potassium borohydride or sodium cyano borohydride, all of which can be used in solid or powdered form, or their aqueous or methanolic solution.

After filtering out the insoluble inorganic substance(s) particles from the reaction mixture eraporation of the filtrate a mixture of epimeric alcohols having general formula (III) and (I)—wherein the meanings of R, $R^1$, $R^2$, $R^3$, and $R^4$ are as given above—is obtained. From this mixture the desired α,β-unsaturated alcohol of (general formula (I) can be isolated by applying the known separation methods for example by chromatography on a silica gel column. If desired the isolated isolated α,β-unsaturated alcohol of general formula (I) can be further purified by crystallization.

The following examples are intended to provide those of ordinary skill in the art with a complete disclosure and description of how to conduct the present synthetic process, and are not intended to limit the scope of this invention.

EXAMPLES

Example 1

To 10 ml of an an hydrous solution prepared by dissolving 1130 mg of (1S,5R,6R,7R)-6-[(E)-2-bromo-5-cyclohexyl-3-oxo-1-pentenyl]-7-(4-phenyl-benzoyloxy)-2-oxabicyclo[3.3.0]octane-3-one in chloroform 1,5 g silica gel with particle size 63–200 µm/Silicagel 60, Merck Cat No 107734/ was added. During rigorous stirring of the obtained mixture at 19–20° C. the solution prepared by dissolving 114 mg of sodium borohydride in 0,22 ml of water was added and stirring was continued intensively for further 60 minutes. The reaction mixture was cooled below 0° C., and the excess reducing agent was reacted with 1,5 ml 2N hydrochloric acid solution. After stirring for 5 minutes 2 ml methanol was added to the mixture and after stirring for further 5 minutes the silica gel was filtered out. Silicagel was washed twice in succession with 3 ml chloroform-methanol mixture of 5:1 volume ratio. The filtrate was flusted with ethyl acetate into a 25 ml volumetric flask and this flask was filled up to the mark with ethyl acetate. The proportion of the produced epimer alcohols, the (1S,5R,6R,7R)-6-[(E)-2-bromo-5-cyclohexyl-3(S)-hydroxy-1-pentenyl]-7-(4-phenyl-benzoyloxy)-2-oxabicyclo[3.3.0]octane-3-one and the 3(R)-hydroxy epimer is 83:17 as determined by HPLC (Nova-Pac Silica 4 µm, 150×3,9 cm column, mobile phase n-hexane and ethanol in 94:6 volume ratio). After evaporation of above solution, the main product the 3(S)-hydroxy epimer was obtained with 75% yield, by isolating it in a column filled with silica gel, and applying a mixture of toluene and ethyl acetate as mobil phase. The obtained crystalline substance melted at 127–129° C., crystallized from the mixture of toluene and n-hexane.

Analysis on the base of molecular formula $C_{31}H_{35}BrO_5$;
Calculated: C, 76,20%; H, 7,43%;
Found: C, 75,96%; H, 7,44%.

Example 2

The process was carried out analogously to Example 1 but as starting α,β-unsaturated keton (1S,5R,6R,7R)-6-[(E)-5-cyclohexyl-3-oxo-1-pentenyl]-7-(4-phenyl-benzoyloxy)-2-oxabicyclo[3.3.0]octane-3-one was applied. The proportion of the produced epimeric alcohols, (1S,5R,6R,7R)-6-[(E)-5-cyclohexyl-3(S)hydroxy-1-pentenyl]-7-(4-phenyl-benzoyloxy)-2-oxabicyclo[3.3.0]octane-3-one and the 3(R)-hydroxy epimer was 77:23 and from the mixture the 3(S)-hydroxy epimer was obtained in 72% yield using column chromatography.

Analysis on the base of molecular formula $C_{31}H_{36}O_5$;
Calculated: C, 76,20%; H, 7,43%;
Found: C, 75,96%, H, 7,44%.

Example 3

The process was carried out analogously to Example 1 but as starting α,β-unsaturated keton (1S,5R,6R,7R)-6-[(E)-4-cyclohexyl-3-oxo-1-butenyl]-7-(4phenyl-benzoyloxy)-2-oxabicyclo[3.3.0]octane-3-one was applied. The ratio of the formed epimeric alcohols, the (1S,5R,6R,7R)-6-[(E)-4-cyclohexyl-3(S)-hydroxy-1-butenyl]-7-(4-phenyl-benzoyloxy)-2-oxabicyclo[3.3.0]octane-3-one and its 3(R)-hydroxy epimer was 75:25. The main component which was obtained in 73% yield was prepared by chromatography using a column filled with silica gel. The obtained crystalline substance melted at 92–94° C., crystallized from a mixture of ethyl acetate, diisopropyl ether and n-hexane.

Analysis on the base of molecular formula $C_{30}H_{34}O_5$;
Calculated: C, 75,92%; H, 7,22%;
Found: C, 76,14%; H, 7,19%

Example 4

The process was carried out analogously to Example 1 but as the starting α,β-unsaturated keton (1S,5R,6R,7R)-6-[(E)-4cyclopentyl-3-oxo-1-butenyl]-7-(4-phenyl-benzoyloxy)-2-oxabicyclo[3.3.0]octane-3-one was applied. The ratio of the formed epimeric alcohols, the (1S,5R,6R,7R6-[(E)-4-cyclopentyl-3(S)hydroxy-1-butenyl]-7-(4-phenyl-benzoyloxy)-2-oxabicyclo[3.3.0]octane-3-one and its 3(R)-hydroxy epimer was 76:24. The main component which was obtained in 71% yield was prepared by chromatography using a column filled with silica gel.

Analysis on the base of molecular formula $C_{29}H_{32}O_5$;
Calculated: C, 75,63%; H, 7,00%;
Found: C, 75,81%; H, 6,88%.

Example 5

The process was carried out analogously to Example 1 but (1S,5R,6R,7R)-6-[(E)-4-phenoxy-3-oxo-1-butenyl]-7-(4- phenyl-benzoyloxy)-2-oxabicyclo[3.3.0]octane-3-one was applied as starting material. The ratio of the formed epimeric alcohols, the (1S,5R,6R,7R)-6-[(E)-4-phenoxy-3(S)-hydroxy-1-butenyl]-7-(4-phenyl-benzoyloxy)-2-oxabicyclo[3.3.0]octane-3-one and its 3(R) hydroxy epimer was 61:39. The main component which was obtained in 58% yield was prepared by chromatography using a column filled with silica gel. The obtained crystalline substance melted at 131–132° C. crystallized from the mixture of ethyl acetate, diisopropylether and n-hexane.

Analysis on the base of molecular formula $C_{30}H_{28}O_6$;

Calculated: C, 74,36%, H, 5,82%;

Found: C, 74,18%; H, 5,91%.

Example 6

The process was carried out analogously to Example 1 but (1S,5R,6R,7R)-6-[(E)-4-(m-chloro-phenoxy)-3-oxo-1-butenyl]-7-(4-phenyl-benzoyloxy)-2-oxabicyclo[3.3.0]octane-3-one was applied as starting material. The ratio of the formed epimeric alcohols, the (1S,5R,6R,7R)-6-[(E)-4-(m-chloro-phenoxy)-3(S)-hydroxy-1-butenyl]-7-(4-phenyl-benzoyloxy)-2-oxabicyclo[3.3.0]octane-3-one and its 3(R)-hydroxy epimer was 58:42. The main component which was obtained in 56% yield was prepared by chromatography using a column filled with silica gel. The obtained crystalline substance melted at 105–108° C. crystallized from the mixture of ethyl acetate and diisopropylether.

Analysis on the base of molecular formula $C_{30}H_{27}ClO_6$;

Calculated: C, 69,43%; H, 5,24%; Cl, 6,83%

Found: C, 69,62%; H, 5,20%. Cl, 6,91%.

Example 7

The process was carried out analogously to Example 1 but (1S,5R,6R,7R)-6-[(E)-5-phenyl-3-oxo-1-pentenyl]-7-(4-phenyl-benzoyloxy)-2-oxabicyclo[3.3.0]octane-3-one was applied as starting material. The ratio of the formed epimeric alcohols, the (1S,5R,6R,7R)-6-[(E)-5-phenyl-3(S)-hydroxy-1-pentenyl]-7-(4-phenylbenzoyloxy)-2-oxabicyclo[3.3.0]octane-3-one and its 3(R)-hydroxy epimer was 76:24. The main component which was obtained in 69% yield was prepared by chromatography using a column filled with silica gel. The obtained crystalline substance melted at 131–132° C. crystallized from the mixture of ethyl acetate and diisopropylether.

Analysis on the base of molecular formula $C_{31}H_{30}O_5$;

Calculated: C, 77,16%; H, 6,27%;

Found: C, 76,94%; H, 6,27%.

Example 8

The process was carried out analogously to Example 1 but (1S,5R,6R,7R)-6-[(E)-4,4-dimethyl-3-oxo-1-octenyl]-7-(4-phenyl-benzoyloxy)-2-oxabicyclo[3.3.0]octane-3-one was used as starting material. The ratio of the formed epimeric alcohols, the (1S,5R,6R,7R6-[(E)-4,4-dimethyl-3(S) hydroxy-1-octenyl]-7-(4-phenyl-benzoyloxy)-2-oxabicyclo[3.3.0]octane-3-one and its 3(R)-hydroxy epimer was 79:21. The main component which was obtained in 70% yield was prepared by chromatography using a column filled with silica gel. The obtained crystalline substance melted at 113–114° C. crystallized from the mixture of diisopropylether and n-hexane.

Analysis on the base of molecular formula $C_{30}H_{36}O_5$;

Calculated: C, 75,60%; H, 7,61%;

Found: C, 75,75%; H, 7,49%.

Example 9

The process was carried out analogously to Example 1 but (1S,5R,6R,7R)-6-[(E)-4,4-dimethyl-3-oxo-1-octenyl]-7-methyl-2-oxabicyclo[3.3.0]octane-3-one was applied as starting material. The ratio of the formed epimeric alcohols, the (1S,5R,6R,7R)-6-[(E)-4,4-dimethyl-3(S)-hydroxy-1-octenyl]-7-methyl-2-oxabicyclo[3.3.0]octane-3-one and its 3(R)-hydroxy epimer was 80:20. The main component which was obtained in 79% yield was prepared by chromatography using a column filled with silica gel.

Analysis on the base of molecular formula $C_{18}H_{30}O_3$;

Calculated: C, 73,43%; H, 10,27%;

Found: C, 73,39%; H, 10,32%.

Example 10

The process was carried out analogously to Example 1 but (1S,5R,6R,7R)-6-[(E)-3-oxo-1-octenyl]-7-(4phenyl-benzoyloxy)-2-oxabicyclo[3.3.0]octane-3-one was used as starting material. The ratio of the formed epimeric alcohols, the (1S,5R,6R,7R)-6-[(E)-3(S)-hydroxy-1-octenyl]-7-(4-phenyl-benzoyloxy)-2-oxabicyclo[3.3.0]octane-3-one and its 3(R)-hydroxy epimer is 74:26. The main component which was obtained in 68% yield was prepared by chromatography using a column filled with silica gel. The obtained crystalline substance melted at 64–67° C. crystallized from the mixture of diisopropylether and n-hexane.

Analysis on the base of molecular formula $C_{28}H_{32}O_5$;

Calculated: C, 74,98%; H, 7,19%;

Found: C, 75,21%; H, 7,43%.

Example 11

The process was carried out analogously to Example 10 but solid lithium borohydride was used instead of aqueous sodium borohydride solution as reducing agent. The ratio of the formed epimeric alcohols was 60:40%. The main component (1S,5R,6R,7R)-6-[(E)-3(S)-hydroxy-1-octenyl]-7-(4phenyl-benzoyloxy)-2-oxabicyclo[3.3.0]octane-3-one was prepared by column chromatography. The thus obtained product did not show any decrease of melting point when it was mixed in discretional ratio with the product prepared according to example 10.

Example 12

The process was carried out analogously to Example 10 but solid potassium borohydride was used as reducing agent instead of sodium borohydride solution, a 72:28 ratio mixture of aqueous 3(S)- and 3(R) epimeric alcohols was obtained, from which the epimeric 3(S)-alcohol was prepared by chromatography. The thus obtained product did not show any decrease of melting point when it was mixed in discretional ratio with the product prepared according to examples 10 or 11.

Example 13

The process was carried out analogously to Example 11 but sodium trimethoxyboro-hydride was used instead of lithium borohydride, a 67:33 ratio mixture of epimeric 3(S)- and 3(R) alcohols was obtained, from which the main product was prepared by chromatography. The thus obtained product did not show any decrease of melting point when it was mixed in discretional ratio with the product prepared according to example 10.

Example 14

The process was carried out analogously to Example 10 but carbon tetrachloride was used as solvent instead of chloroform, a 75:25 ratio mixture of epimeric alcohols was obtained, from which the main product, (1S,5R,6R,7R)[(E)-3(S)-hydroxy-1-octenyl]-7-(4-phenyl-benzoyloxy)-2-oxabicyclo[3.3.0]octane-3-one—produced with 40% yield—was prepared by column chromatography. The thus obtained product did not show any decrease of melting point when mixed in discretional ratio with the product prepared according to example 10.

Example 15

The process was carried out analogously to Example 14 but toluene was used as solvent instead of carbon tetrachloride, a 74:26 ratio mixture of epimeric alcohols was obtained, from which the 3(S)-alcohol—produced with 57% yield—was prepared by column chromatography. The thus obtained product did not show any decrease of melting point when it was mixed in discretional ratio with the product prepared according to example 10.

Example 16

The process was carried out analogously to Example 14 but methylene chloride was used as solvent, a 73:28 ratio mixture of epimeric 3(S)- and 3(R) alcohols was obtained, from which the 3(S)-alcohol—produced with 63% yield—was prepared by column chromatography.

Example 17

The process was carried out analogously to Example 14 but acetonitrile was used as solvent, a 60:40 ratio mixture of epimeric 3(S)- and 3(R) alcohols was obtained, from which the 3(S)-alcohol—produced with 48% yield—was prepared by column chromatography processing.

Example 18

The process was carried out analogously to Example 14 but tetrahydrofurane was used as solvent, a 61:39 ratio mixture of epimeric 3(S)- and 3(R) alcohols was obtained, from which the 3(S)-alcohol—produced with 45% yield—was prepared by column chromatography.

Example 19

The process was carried out analogously to Example 14 but ethyl acetate was used as solvent, a 70:30 ratio mixture of epimeric 3(S)- and 3(R) alcohols was obtained, from which the 3(S)-alcohol—produced with 53% yield—was prepared by column chromatography.

Neither of the products prepared according to examples 16.,17.,18., and 19,showed any decrease of melting point when they were mixed in discretional ratio with the product prepared according to example 10.

Example 20

The process was carried out analogously to Example 10 but silica gel of 40–63 µm particle size/"Silicagel 60" Merck Cat. No. 109385/was used. From the formed mixture of epimeric 3(S)- and 3(R) alcohols (ratio was 62:26) the main product was obtained by chromatography. It did not show any decrease of melting point when it was mixed in discretional ratio with the product prepared according to example 10.

Example 21

The process was carried out analogously to Example 10 but silica gel of 5–40 µm particle size/"Silicagel G" Merck Cat. No. 10773 1/was used. From the formed mixture of epimeric 3(S) and 3(R) alcohols (ratio 62:26) the main product was obtained by chromatography. It did not show any decrease of melting point when it was mixed in discretional ratio with the product prepared according to example 10.

Example 22

The process was carried out analogously to Example 10 but Brockmann I acidic aluminium oxide/Aldrich Cat.No. 19996-6/was used instead of silica gel. From the formed mixture of epimeric 3(S) and 3(R) alcohols (ratio was 33:13) the main product was obtained by chromatography. It did not show any decrease of melting point when it was mixed in discretional ratio with the product prepared according to example 10.

Example 23

The process was carried out analogously to Example 10 but Brockmann I basic aluminium oxide/Aldrich Cat.No. 19944-3/was used instead of silica gel . From the formed mixture of epimeric 3(S)- and 3(R) alcohols (ratio was 2:1) obtain the main product by chromatography. It did not show any decrease of melting point when it was mixed in discretional ratio with the product prepared according to example 10.

Example 24

The process was carried out analogously to Example 10 but Brockmann I neutral aluminium oxide/Aldrich Cat.No. 19997-4/was used instead of silica gel. From the formed mixture of epimeric 3(S)- and 3(R) alcohols (ratio was 2.5:1.4) obtain the main product by chromatography. It did not show any decrease of melting point when it was mixed in discretional ratio with the product prepared according to example 10.

What is claimed is:

1. A process for the preparation of α,β-unsaturated alcohols of the formula (I):

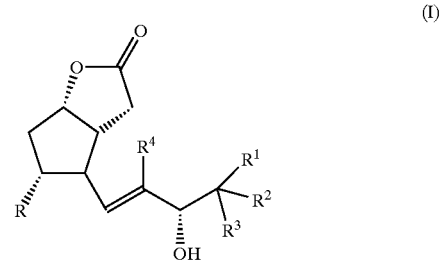

(I)

wherein

R is an alkyl group of 1–4 carbon atoms, or a benzoyloxy group optionally substituted with a phenyl group;

$R^1$ is a hydrogen atom or an alkyl group of 1–4 carbon atoms;

$R^2$ is a hydrogen atom or an alkyl group of 1–4 carbon atoms;

$R^3$ is an alkyl group of 1–6 carbon atoms, optionally substituted by a phenyl group or a cycloalkyl group of 5–7 carbon atoms; a phenoxy group optionally substituted by a halogen atom, or a cycloalkyl group of 5–7 carbon atoms;

$R^4$ is a hydrogen atom or a halogen atom, wherein an α,β-unsaturated ketone of formula (II)

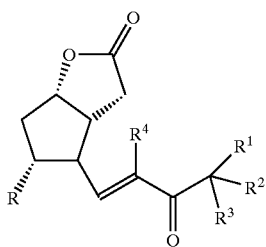
(II)

wherein R, R¹, R², R³, and R⁴ are as defined above is diastereoselectively reduced with a borohydride type compound in an aprotic solvent, in the presence of an inorganic substance insoluble in the reaction mixture selected from the group consisting of silica gel and aluminum oxide and having a particle size ranging from 0.01 micrometer to 10,000 micrometer to yield a mixture of epimeric α,β-unsaturated alcohols of formula (I) and (III):

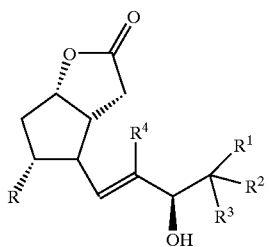
(III)

wherein R, R¹, R², R³, and R⁴ are as defined above, and optionally separating the α,β-unsaturated alcohol of formula (I) from said mixture.

2. A process according to claim 1 wherein said aprotic solvent comprises a halogenated hydrocarbon.

3. A process according to claim 2 wherein said halogenated hydrocarbon is selected from the group consisting of carbon tetrachloride, chloroform, and methylenechloride.

4. A process according to claim 1 wherein said aprotic solvent comprises an aliphatic carboxylic acid ester.

5. A process according to claim 4 wherein said aliphatic carboxylic acid ester comprises ethyl acetate.

6. A process according to claim 1 wherein said aprotic solvent comprises an ether-type solvent.

7. A process according to claim 6 wherein said aprotic ether-type solvent comprises tetrahydrofuran.

8. A process according to claim 1 wherein said aprotic solvent comprises a hydrocarbon.

9. A process according to claim 8 wherein said hydrocarbon is selected from the group consisting of toluene and xylene.

10. A process according to claim 1 wherein said aprotic solvent comprises an alkylnitrile.

11. A process according to claim 10 wherein said alkylnitrile comprises acetonitrile.

12. A process according to claim 1 wherein said cosolvent containing short carbon chains is selected from the group consisting of methanol and ethanol.

13. A process according to claim 1 wherein said borohydride type compound comprises an alkali-trialkoxy-borohydride.

14. A process according to claim 1 wherein said alkali-trialkoxy-borohydride comprises sodium-trimethoxy-borohydride.

15. A process according to claim 1 wherein said borohydride type compound comprises an alkali borohydride.

16. A process according to claim 15 wherein said alkali borohydride is selected from the group consisting of lithium borohydride, sodium borohydride and potassium borohydride.

17. A process according to claim 1 wherein a silica gel is used having a particle size ranging from 1 μm to 1000 μm.

18. A process according to claim 1 wherein said inorganic substance is selected from the group consisting of an activated, acidic, basic and neutral aluminum oxide.

* * * * *